United States Patent [19]

Omura et al.

[11] 4,194,064
[45] Mar. 18, 1980

[54] PRODUCTION OF NANAOMYCIN B

[75] Inventors: Satoshi Omura, Tokyo; Haruo Tanaka, Machida; Juichi Awaya, Souka; Toju Hata, Tokyo, all of Japan

[73] Assignee: The Kitasato Institute (Kitasato Kenkyusho), Tokyo, Japan

[21] Appl. No.: 858,216

[22] Filed: Dec. 7, 1977

Related U.S. Application Data

[63] Continuation of Ser. No. 719,752, Sep. 2, 1976, abandoned, which is a continuation-in-part of Ser. No. 558,514, Mar. 14, 1975, abandoned.

[30] Foreign Application Priority Data

Apr. 15, 1976 [JP] Japan .............................. 51-42881

[51] Int. Cl.$^2$ .............................................. C12D 9/14
[52] U.S. Cl. ................................... 435/125; 435/127; 435/132; 435/146; 435/147; 435/156; 435/169; 435/886; 260/345.2; 424/181
[58] Field of Search .................... 195/80 R, 81, 96; 260/345.2; 424/181

[56] References Cited

U.S. PATENT DOCUMENTS

| | | | |
|---|---|---|---|
| 3,817,835 | 6/1974 | Neidleman | 195/80 R |
| 3,833,556 | 9/1974 | Shier et al. | 195/80 R |
| 4,003,902 | 1/1977 | Kluepfel et al. | 195/81 X |
| 4,036,696 | 7/1977 | Stapley et al. | 195/80 R |

OTHER PUBLICATIONS

Tanaka et al., Nanaomycins, New Antibiotics Produced by a Strain of Streptomyces, Journal of Antibiotics, vol. 28, No. 12, 1975, (pp. 925-930).

Primary Examiner—David M. Naff
Attorney, Agent, or Firm—Wolder, Gross & Yavner

[57] ABSTRACT

The present invention relates to new compound designated as nanaomycin B represented by general formula:

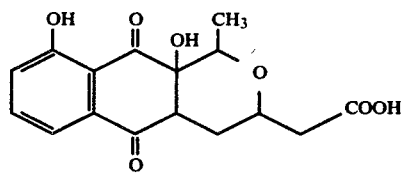

Nanaomycin B is a quinone type and is active on mycoplasma, Gram-positive bacteria and trycophyton. This compound is useful as a medicament for infectious diseases of humans and animals caused by a parasite of trichophyton or mycoplasma etc. The acute toxicity ($LD_{50}$, intra-penetrial injection) in mice of this compound is 169 mg/kg. Nanaomycin B is produced by fermentation in which a nanaomycin-producing strain belonging to the genus Streptomyces is cultured in a medium under aerobic conditions and the accumulated nanaomycin B in the cultured broths is recovered therefrom.

4 Claims, 2 Drawing Figures

PRODUCTION OF NANAOMYCIN B

RELATED APPLICATION

This application is a continuation of application Ser. No. 719,752, filed Sept. 2, 1976, which is a continuation-in-part of application Ser. No. 558,514, filed Mar. 14, 1975, both now abandoned.

SUMMARY OF THE INVENTION

The present invention relates to new compound designated as nanaomycin B as well as to a process for producing the same by fermentation.

Nanaomycin B is also designated as OS-3966-B or Rosanomycin B and represented by general formula:

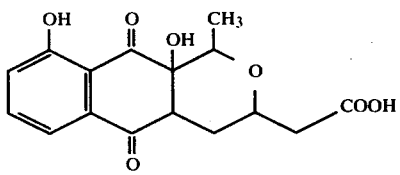

The above-mentioned formula has been determined by various experiments including nuclear magnetic resonance spectra, elementary analysis, mass-spectra and the like.

DRAWINGS

Figure 1:
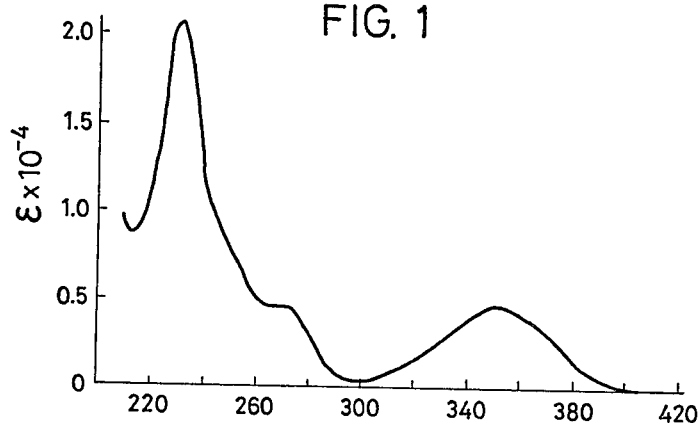
Figure 2:
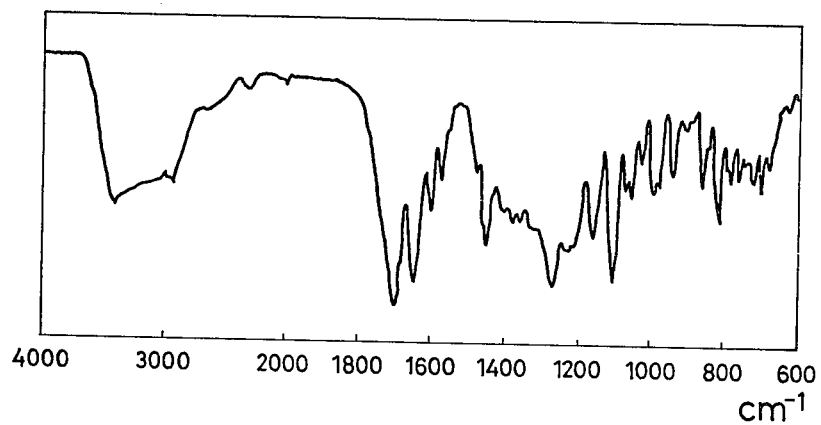

FIGS. 1 and 2 show UV and IR absorption spectra of nanaomycin B, respectively.

Nanaomycin B is in the form of pale-yellow powder and has the following physical and chemical characteristics:

1. Elementary analysis:
   Found: C - 59.70%; H - 4.90%; N - 0%. Calculated (as $C_{16}H_{16}O_7$): C - 59.99%; H - 5.03%; N - 0%.
2. Molecular weight:
   m/e determined by mass spectrum is 320.090 and the theoretical value of m/e for $C_{16}H_{16}O_7$ is 320.090.
3. Melting point: About 84°-86° C.
4. Specific rotation: $[\alpha]_D^{26} -74.5°$ (C - 1.0, methanol)
5. Ultraviolet absorption spectrum (FIG. 1):
   $_{max}^{MEOH}$ nm($\epsilon$): 231 (2.08×10$^4$), 248 (shoulder) (0.870×10$^4$), 269 (shoulder) (0.503×10$^4$), 352 (0.497×10$^4$)
6. Infrared absorption spectrum (FIG. 2):
   Specific, comparatively strong absorptions at 3500 - 2900, 1705, 1648, 1605, 1450, 1380, 1355, 1268, 1210 - 1240, 1160 and 1107 cm$^{-1}$ (by KBr method)
7. Solubility:
   Easily soluble in methanol, ethanol, ethylacetate, chloroform, acetone and ether. Insoluble in n-hexane, petroleum ether and water.
8. Color reaction:
   Positive in the reactions with ferric chloride and reduction catalyst. [Feigl, N., Anal. Chem., 28, 397 (1956)]. Negative in ninhydrin reaction, Sakaguchi reaction, Ehrlich reaction, Fehling reaction and Molish reaction.

As is apparent from the foregoing characteristics, nanaomycin B is considered to be a quinone type compound which is, however, not identified with any known compounds. Accordingly, it has been confirmed that nanaomycin B is a new compound.

The antimicrobial spectra of nanaomycin B is shown in Table 1.

As is apparent from the foregoing characteristics, nanaomycin B is considered to be a quinone type compound which is however not identified with any known compounds. Accordingly, it has been confirmed that nanaomycin B is a new compound.

The antimicrobial spectra of nanaomycin B is shown in Table 1.

Table 1

| Test organisms | Medium | MIC (µg/ml) |
|---|---|---|
| *Bacillus subtilis* PCI 219 | N | 7.8 |
| *Staphylococcus aureus* FDA 209P | N | 3.9 |
| *Staphylococcus aureus* FDA 209P (JC-1) | N | 2.0 |
| *Sarcina lutea* PCI 1001 | N | 2.0 |
| *Mycobacterium smegmatis* | N | 125 |
| *Escherichia coli* NIHJ | N | 15.6 |
| *Escherichia coli* NIHJ (JC-2) | N | 500 |
| *Klebsiella pneumoniae* PCI 602 | N | 31.3 |
| *Salmonella typhimurium* | N | 62.5 |
| *Shigella flexneri* | N | 62.5 |
| *Xanthomonas oryzae* N-5824 | N | 125 |
| *Pseudomonas aeruginosa* | N | >500 |
| *Candida albicans* | P | 31.2 |
| *Saccharomyces sake* | P | 62.5 |
| *Aspergillus niger* ATCC 6275 | P | 62.5 |
| *Aspergillus fumigatus* IAM 2612 | P | >100 |
| *Piricularia oryzae* | P | 15.6 |
| *Microsporum gypseum* 704 | P | 12.5 |
| *Trichophyton asteroides* | P | 12.5 |
| *Trichophyton ferrugineum* | P | 12.5 |
| *Trichophyton interdigitale* | P | 12.5 |
| *Trichophyton mentagrophytes* | P | 25 |
| *Trichophyton pedis* 804 | P | 3.1 |
| *Trichophyton purpureum* | P | 25 |
| *Trichophyton roseum* | P | 12.5 |
| *Trichophyton rubrum* | P | 3.1 |
| *Trichophyton schoenleini* | P | 3.1 |
| *Trichophyton violaceum* | P | 3.1 |
| *Mycoplasma gallisepticum* KP-13 | H | <0.013 |
|  | E | 0.10 |
| *Mycoplasma gallisepticum* S-6 | H | <0.013 |
|  | E | 0.10 |
| *Mycoplasma gallisepticum* 333P (Spiramycin resistant) | H | 0.013 |
|  | E | 0.05 |
| *Mycoplasma gallinarum* | H | 3.12 |
| *Mycoplasma iners* | H | 3.12 |
| *Mycoplasma pneumonia* | E | 0.05 |
| *Acholeplasma laidlaw* (A) PG8 | H | >25 |
|  | E | >25 |
| *Acholeplasma laidlawii* (B) Bml | H | 25 |
|  | E | >25 |

Note:
Medium N - nutrient agar (pH 7.0, 2 days. 37° C.)
P - potato agar (pH 6.4, 4 days. 27° C.)
H - Hokken PPLO agar (pH 7.8, 8 days. 37° C.)
E - Eiken PPLO agar (pH 7.8, 8 days. 37° C.)
MIC - Minimal inhibitory concentration As is shown in Table 1, nanaomycin B has a high activity against mycoplasma. For example, the growth of *Mycoplasma gallisepticum* is inhibited by nanaomycin B at a concentration of not more than 0.1 µg/ml. A high antimicrobial activity on nanaomycin B on a spiramycin-resistant *Mycoplasma gallisepticum* is observed. Also, nanaomycin B inhibit the growth of Gram-positive bacteria such as, for example *Staphylococcus aureus* at a concentration of 2.0 to 8.0 µg/ml and the growth of various fungi of some species belonging to the genus *Trichophyton* at a concentration of not more than 25.0 µg/ml.

An excellent therapeutic effect is exhibited by nanaomycin B on various infectious diseases caused by a parasite of the genus *Tricophyton* in the body of animals. When dermatomycosis caused by *Tricophyton metagro-*

*phytes* at the back of guinea pigs is treated by applying a solution of 0.01–1% nanaomycin B dissolved in propylene glycol-ethanol (3:1 v/v) once daily for 8 days, an excellent therapeutic effect on erythema and scales is observed. Nanaomycin B has furthermore a therapeutic effect on various diseases of human and animals, and its therapeutic effect on a chronic respiratory disease of chickens caused by *Mycoplasma gallisepticum* is observed.

When dermatomycosis of cattle caused by mass infection of *Trichophyton verrucosum* is treated with nanaomycin B, nanaomycin B is dissolved or suspended in a suitable carrier, for example, olive oil, and is coated on the affected part directly with or without removal of the scales. SP-Burton, a commercial product available from Rakuno-shinko K.K., Japan, which is considered as a most effective agent for dermatomycosis of animals, is used as a control therapeutic agent. The therapeutic effects are observed for four weeks. The results obtained by coating nanaomycin B once and by twice coatings (the second coating is carried out a week after the first coating) are shown in tables 2 and 3, respectively.

Table 2

| | | | Result AFTER | | | |
|---|---|---|---|---|---|---|
| Agent | Con. mg/ml | Sample | 1 week | 2 weeks | 3 weeks | 4 weeks |
| Nanaomycin B | 0.1 | 1 | ++ | ++ | +++ | +++ |
| I Nanaomycin B | 1 | 1 | ++++++ | +++ | +++ | |
| Nanaomycin B | 10 | 1 | ++++++ | +++ | +++ | |
| SP-Burton | 0.3 | 1 | — | — | — | — |
| Nanaomycin B | 0.1 | 1 | ++++++ | +++ | +++ | |
| II Nanaomycin B | 1 | 1 | ++++++ | +++ | +++ | |
| Nanaomycin B | 10 | 1 | ++++++ | +++ | +++ | |
| SP-Burton | 0.3 | 1 | ++++ | — | — | |

Note:
I - direct coating on affected part
II - coating after removing the scales of affected part
Con. - concentration of agent
+ + + - complete removal of scales and recovered
+ + - a little scales remained
+ - removal of a part of scales
— - no removal of scale and no recovery Table 3

| | | | Result AFTER | | | |
|---|---|---|---|---|---|---|
| Agent | Con. mg/ml | Sample | 1 week | 2 weeks | 3 weeks | 4 weeks |
| Nanaomycin B | 0.1 | 1 | ++ | +++ | +++ | +++ |
| I Nanaomycin B | 1 | 1 | ++ | ++ | +++ | +++ |
| Nanaomycin B | 10 | 1 | ++++++ | +++ | +++ | |
| SP-Burton | 0.3 | 1 | — | — | — | — |
| Nanaomycin B | 0.1 | 1 | ++++++ | +++ | +++ | |
| II Nanaomycin B | 1 | 1 | ++++++ | +++ | +++ | |
| Nanaomycin B | 10 | 1 | ++++++ | +++ | +++ | |

Table 3-continued

| | | | Result AFTER | | | |
|---|---|---|---|---|---|---|
| Agent | Con. mg/ml | Sample | 1 week | 2 weeks | 3 weeks | 4 weeks |
| SP-Burton | 0.3 | 1 | +++++ | + | — | |

Note:
I - direct coating on affected part
II - coating after removing the scales of affected part
Con. - concentration of agent
+ + + - complete removal of scales and recovered
+ + - a little scales remained
+ - removal of a part of scales
— - no removal of scale and no recovery The antifungal activity of nanaomycin B is shown in Table 4, in which the antifungal activity of nanaomycin B is superior to that of the known antibiotic ethylkalafunginate (ethylkalamycinate) though slightly inferior to that of the known compound of deoxyfrenolicin. Nanaomycin B exhibits stronger antifungal activity when the pH of the medium is higher than 6.4 shown in Table 4.

Table 4

| | Antifungal Activity | | |
|---|---|---|---|
| | Minimal Inhibitory Con. ($\mu$g/ml) | | |
| Test Organisms | Nanaomycin B | Y | Z |
| *Candida albicans* | >100 | 50 | >100 |
| *Saccharomyces sake* | >100 | 6.3 | >100 |
| *Aspergillus fumigatus* | 50 | 6.3 | >100 |
| *Aspergillus niger* | >100 | >100 | >100 |
| *Microsporum gypseum* | 12.5 | <0.2 | >100 |
| *Trichophyton asteroides* | 12.5 | <0.2 | >100 |
| *Trichophyton femungineum* | 6.3 | 3.1 | >100 |
| *Trichophyton interdigitale* | 12.5 | 0.4 | >100 |
| *Trichophyton rubrum* | 6.3 | <0.2 | >100 |
| *Trichophyton schoenleini* | 0.4 | <0.2 | >100 |
| *Trichophyton violaceum* | 6.3 | 0.8 | >100 |

Note:
Minimal inhibitory concentration is assayed by agar dilution method (potato agar, pH 6.4, 27° C., 4 days)
Y - deoxyfrenolicin
Z - ethylkalafunginate (ethylkalamycinate)

Table 5 shows the antimycoplasma activity of nanaomycin B, which is superior to those of ethylkalafunginate and deoxyfrenolicin.

Table 5

| | Antimycoplasma Activity | |
|---|---|---|
| Antibiotic | Concentration ($\mu$g/ml) | Inhibitory Zone (mm) |
| Nanaomycin B | 10 | 22.7 |
| | 100 | 32.6 |
| Deoxyfrenolicin | 10 | 14.6 |
| | 100 | 21.8 |
| Ethylkalfunginate | 10 | none |
| | 100 | none |

Note:
Inhibitory zone is assayed by paper disc method (Eiken PPLO agar, pH 7.8, 37° C., 1 day).

As apparent from the above tables, nanaomycin B exhibits an especially strong activity on mycoplasma, and is also active on Gram-positive bacteria and trycophyton. Accordingly, it can be said that nanaomycin B represents a new antibiotic which may be used as a medicament for human beings and animals. $LD_{50}$ of nanaomycin B (determined by intra-penetrial injection into mouse) is 169 mg/Kg.

According to another aspect of the present invention, there is provided a process for producing nanaomycin B, characterized by the fact that a microorganism which belongs to the genus *Streptomyces* and which is capable of producing nanaomycin B is cultured aerobically in a medium to accumulate nanaomycin B in the cultured broths and the accumulated nanaomycin B is then recovered therefrom.

For the purpose of the present invention, it is possible to use not only the hereinafter described *Streptomyces rosa var. notoensis* and any mutant obtained therefrom but also any strain which belongs to the genus *Streptomyces* and which is capable of producing nanaomycin B. The microbiological characteristics of a preferable strain *Streptomyces rosa var. notoensis* which is used in the following examples to produce nanaomycin B are as follows:

1. Morphological characteristics:
   Forming abundantly aerial mycelium on both synthetic and natural agar media, the ending of which forming massy or irregular spiral. Conidiophore formed on aerial mycelium. Conidiospores are oval (0.6 –1.0μ) and in a chain of 10 or more. The spores have smooth surfaces.
2. Cultural characteristics:
   Shown in Table 6.

The microbiological characteristics of this strain are summarized as follows:

Conidiophore is spiral and conidiospore is smooth. Growth on synthetic medium is colored in yellowish gray or orange or reddish brown, and the formed aerial mycelium is colored in white or orange gray or pink. There is formed a soluble pigment colored in yellowish brown or dark reddish brown. When an organic medium is used, the growth is generally colorless or colored in orange gray or brown, and the formed mycelium is colored in white or orange gray or pink. Sometimes soluble pigment is not formed, while a greenish gray or grayish black pigment is formed in some media. This strain is non-chromogenic and has a relatively high activity with regard to the decomposition of protein and starch.

With respect to the strains having the aforementioned characteristics, a search was made for strains having analogous characteristics to those of the strain used in the following examples with reference, for example, to "The Actinomycetes" by S. A. Waksman, Vol. 2 (1961) and "Cooperative Description of Type Strains of Streptomyces" by E. B. Shirling and D. Gottlieb [Interna- Table 6

Cultural Characteristics of S. rosa var. notoensis(FERM 2209)

| Medium | Growth | Reverse | Aerial mycelium | Soluble pigment |
|---|---|---|---|---|
| Sucrose-nitrate agar | good, light ivory to light melon yellow | light melon yellow to apricot | light apricot | pearl pink to light melon yellow |
| Glucose-nitrate agar | good, dusty yellow to golden brown | golden brown to chocolate brown | white to pearl pink | light wheat to sepia brown |
| Glycerol-asparagine agar | good, light melon yellow to orange rust | apricot | light apricot | melon yellow to apricot |
| Inorganic salts-starch agar | moderate, light melon yellow | pearl pink to golden brown | white to flesh pink | dark lumage tan to sepia brown |
| Tyrosine agar | good, light wheat to amber topaz | light melon yellow to nude tan | light melon yellow to pearl pink | light wheat to melon yellow |
| Nutrient agar | moderate, colorless to pearl pink | squash yellow to bright yellow | white, scant | none |
| Glucose-pepttone agar | moderate, colorless to golden brown | golden brown to sepia brown | white | ivy to dark laurel |
| Yeast extract-malt extract agar | good, colorless to golden brown | golden brown to orange rust | light melon yellow to light apricot | ivy |
| Oatmeal agar | moderate, colorless to light melon yellow | light melon yellow to nude tan | light melon yellow to light apricot | light tan |
| Peptone-yeast extract iron agar | moderate, cream to light wheat | colonial yellow | scant, white to colonial yellow | none |
| Tryptone-yeast extract broth | surface growth, moderate, light ivory | light ivory | white | none |
| Milk | pearl pink | | none | light apricot to pearl pink |
| Gelatin | surface growth, good | pearl pink to chartreuse tint | white to celadon gray | laurel |
| Nitrate broth | surface growth, moderate | light ivory | white | none |
| Cellulose | none | none | none | none |

3. Physiological characteristics:
   Growth temperature: 15°–45° C.
   Liquefaction of gelatin: positive
   Hydrolyzation of starch: positive
   Coagulation of skim milk: positive
   Peptonization of skim milk: positive
   Formation of melanoid pigment: negative
   Formation of tyrosinase: negative
   Reduction of nitrate: positive
   Formation of hydrogen sulfide: negative
   Decomposition of cellulose: negative
4. Usability of various carbon sources:
   Arabinose, xylose, glucose, fructose, rhamnose, mannitol, glycerol, maltose and mannose may be usable; while sucrose, innositol and raffinose may be unusable.

tional Journal of Systematic Bacteriology, Vol. 18, No. 2, pages 69–189 (1968); Vol. 18, No. 4, pages 279–329 (1969); Vol. 9, No. 4, pages 391–512 (1969); and Vol. 22, No. 4, pages 265–394 (1972)]. As a result, some species designated as "fradiae", i.e. *Streptomyces fradiae*, *Streptomyces luridus*, *Streptomyces roseus*, *Streptomyces fuscus*, *Streptomyces roseoluteus*, and *Streptomyces rosa* were found as being analogous. Among them, *Streptomyces roseoluteus* and *Streptomyces rosa* are indeed likely to be most analogous. However, on one hand *Streptomyces roseoluteus* is distinguishable from the nanaomycin-producing strain of the present invention because the color at the reverse side of *S. roseoluteus*'s colony becomes yellowish orange from yellow in certain media such as for example of yeast extract-malt extract, oat meal agar, inorganic starch agar as well as of glycerol-asparagine agar, with simultaneously formation of yellowish soluble pigment. On the other hand, *Streptomyces rosa* is generally similar to the nanaomycin-producing strain according to the present invention with the exception that the production of soluble pigment in a certain media such as for example of yeast extract-malt extract agar, glucose-peptone agar and that the reduction of nitrate is not observed in the case of *Streptomyces rosa*. Accordingly, this strain is designated as *Streptomyces rosa var. notoensis*.

The nanaomycin-producing strain used in the following examples produces simultaneously in the cultured broths nanaomycin B and nanaomycins A and C represented by general formulae:

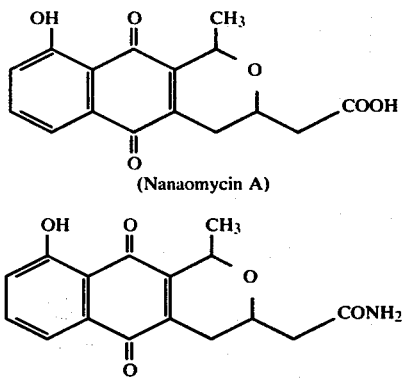

(Nanaomycin A)

and referred to in the related U.S. Pat. application Ser. No. 719,744, filed Sept. 2, 1976, now abandoned The strain used in the following examples has been deposited on an unrestricted basis with the Fermentation Research Institute, Agency of Industrial Science and Technology, Japanese Government, and assigned an accession number of FERM-P No. 2209.

According to the process of the present invention, either any synthetic or organic medium may be used when it contains a suitable carbon source, nitrogen source, inorganic substances and, if desired, various other nutrients. Various carbon and nitrogen sources may be used when these sources are adaptable for the strain in use.

More concretely, the useful carbon sources are exemplified by various carbohydrates such as glucose, glycerol, fructose, maltose, mannitol, xylose, galactose, lactose, ribose, starch and starch hydrolyzate. The concentration of carbon source is preferably 0.5-5.0% (when calculated as glucose) based upon the medium. It is also possible to use organic acids such as, for example, gluconic acid, pyruvic acid, lactic acid, acetic acid; and various amino acids such as glycine, glutamic acid, alanine, etc.

As the nitrogen source, it is possible to use, for example, ammonia; various inorganic and organic ammonium salts such as ammonium chloride, ammonium phosphate, ammonium sulfate, ammonium nitrate; nitrogen-containing organic materials such as urea, peptone, NZ-amine, meat extract, dried yeast, yeast extract, corn steep liquor, casein hydrolyzate, fish meal, digested product thereof, soybean meal, digested products thereof, defatted soybean, digested products thereof, pupa hydrolyzate, and various amino acids such as glycine, glutamic acid, alanine, etc.

As the inorganic substance, it is possible to use, for example, various phosphates, magnesium sulfate, etc. If desired, it is also possible to use a trace amount of heavy metal salts, which is however, not always essential when the medium used contains natural materials. In case a mutant strain having a nutritional requirement is used, it is necessary to add the required substance to the medium.

Liquid medium is preferable for producing large amount of nanaomycins A, B and C, though solid medium may be used. It is possible to use a seed medium having a similar composition to that of the main culture medium, and the seed is preferably obtained by fermentation carried out aerobically at a temperature of 27° C. for two days, for example, by using a Sakaguchi flask.

The fermentation is carried out aerobically with shaking and/or submerged conditions at a temperature of from 15° to 40° C. at an adjusted pH of 6-10 for about 2-8 days, whereby large amounts of nanaomycins A, B and C are accumulated concurrently in the medium and microbial body. After completion of the fermentation, nanaomycins A, B and C are recovered from the cultured broths. For example, the broths are separated into the microbial body and filtrate. The filtrate is adjusted to an acidic pH (preferably from 2 to 4) with HCl or the like and is then subjected to extraction with a suitable organic solvent such as e.g. ethyl acetate or butyl acetate. After this, nanaomycins A, B and C are obtained by purifying the extracted substance in a conventional manner which would be used for the purification of known substances soluble in organic solvents.

According to the present invention, preferable methods for the fermentation are examplified as follows:

A culture medium (100 ml) is put in a 500 ml Sakaguchi flask and sterilized at a temperature of 120° C. for 15 minutes. After this, spores and/or mycelium of the used strain are inoculated and the fermentation is effected with shaking (110 r.p.m.) at a temperature of 27° C. for a sufficient period of time (e.g. for 3 days) to accumulate large amounts of nanaomycins A, B and C in the culture broths.

Alternatively, a culture medium (20 liters) is put into a 30-liter jar fermentor and sterilized at a temperature of 120° C. for 15 minutes. After this, a seed culture is inoculated and the fermentation is effected at a temperature of 27° C. for three days with shaking (300 r.p.m.) and aeration (10 l/min). It is also preferred to culture using a medium (200 ml) in a tank-type fermentor (capacity—400 liters) for three days at 27° C. with shaking (200 r.p.m.) and aeration (100 l/min).

In either case, good results can be obtained by using glycerine and soybean meal as the carbon and nitrogen sources, respectively. A medium containing glycerine (2.0%), soybean meal (2.0%) and NaCl (0.3%) and having a pH of 7.0 is particularly advantageous. In one embodiment using this medium, an inhibition zone (diameter—30 cm) is observed in the supernatant of the cultured liquor at a pH of 5.2 after culturing at a temperature of 27° C. for 70 hours by using a tank-type fermentor. Although nanaomycins A, B and C are found in both the fermented liquid and solid materials, the former contains usually larger amounts of nanaomycins A, B and C than the latter.

After completion of the fermentation, nanaomycins A, B and C are recovered from the cultured broths in the following manner:

The cultured broths are separated into solid and liquid phases in conventional manner by means of filtering, centrifuging and the like. The liquid phase, i.e. the filtrate is adjusted to an acidic pH (preferably from 2 to 4)

with HCl or the like, and is then subjected to extraction with a suitable organic solvent such as e.g. ethyl acetate or butyl acetate. After this, nanaomycins A and B are obtained by purifying the extracted substance in a conventional manner which is applicable for the purification of known substances soluble in organic solvents.

It is also possible to isolate nanaomycins A and B from the extracted solution in an acidic condition. In this case, an excessively higher pH should be avoided to obtain a large amount of nanaomycin B, because nanaomycin B may be converted into nanaomycin A in an alkaline condition. For example, an aqueous solution of sodium bicarbonate (1%) is used to elute nanaomycins A and B from the extract with quick speed. Immediately after this, the eluate containing nanaomycins A and B is adjusted to an acidic pH, for example, with hydrochloric acid and further extracted with a suitable organic solvent such as, for example, ethyl acetate or butyl acetate. The thus-obtained extract is concentrated to dryness, resulting in nanaomycins A and B in the form of crude powders which are then subjected to the column chromatography using silica-gel, whereby the crude powders containing nanaomycins A and B are developed with a solvent system of benzene-acetone (4:1 v/v) to elute the fractions containing nanaomycin A, followed by nanaomycin B-containing fractions. The thus-obtained fractions are separately combined and concentrated to dryness. The dried material containing nanaomycin A is dissolved in ethanol which is then added with a small amount of water to give nanaomycin A in the form of needle crystals.

Nanaomycin B can also be purified in a similar manner to that applied to the purification of nanaomycin A, whereby the combined fractions containing nanaomycin B are concentrated to dryness and then subjected to the silica-gel column chromatography using benzene-acetone (3:1 v/v) as the developer.

In the recovery stated above, nanaomycins A and B are eluted from the ethyl acetate layer with 1% of sodium bicarbonate, while nanaomycin C remains in the ethyl acetate layer because nanaomycin B is neutral, which is then concentrated under reduced pressure to dryness to obtain the crude powders of nanaomycin C. The crude powders are chromatographed on a column of silica-gel with chloroform-methanol (50:1 v/v). The fractions containing nanaomycin C are concentrated under reduced pressure to dryness to obtain crude powders of nanaomycin C which are extracted with ethyl acetate and then recrystallized from an ethyl acetate to obtain orange crystals of nanaomycin C.

Nanaomycins A, B and C are assayed in a similar manner to that designated as the paper disc method by Itoh, et al [J. of Antibiotics, 24, 855–859 (1971)], for example as follows:

The strain is cultured at a temperature of 27° C. with shaking. The medium (pH 7.0) contains glycerine (2.0%), soybean meal (2.0%) and NaCl (0.3%). Inhibition zones of a diameter of 17, 27, 28 and 29 mm are observed in the cultured liquor after culturing for 24, 48, 72 and 96 hours, respectively.

Nanaomycin B is easily converted into nanaomycin A in an alkaline condition and is gradually converted in an acidic or neutral condition. For example, nanaomycin A is obtained from nanaomycin B in an alkaline medium in the following manner:

Nanaomycin B (200 mg) is dissolved in 60 ml of 0.1N sodium hydroxide and the solution is allowed to stand for 10 minutes. After adjusting to pH 2.0 with 6N hydrochloric acid, the product is extracted with ethyl acetate. The extract is evaporated and orange yellow needles are obtained from an ethanol solution of the product. The compound is identified as nanaomycin A by the melting point, IR spectrum and thin-layer chromatography.

Although nanaomycin B itself exhibits no or little activity, nanaomycin B is converted into nanaomycin A in a culture medium or in living bodies, so that its activity exerts gradually. It is accordingly possible to use both nanaomycins B and A for the same purpose.

The following non-limitative examples illustrate the invention.

EXAMPLE 1:

One platinum loop of *Streptomyces rosa* var. *notoensis* FERM-P No. 2209 capable of producing nanaomycins was taken from a slant culture and inoculated to a seed medium (pH 7.0) for culturing at a temperature of 27° C. for 2 days. The resultant seed culture was further inoculated to a medium (20 liters) put in a 30-liter jar fermentor at a ratio of 1% and cultured at 27° C. for 4 days with aeration (10 l/min) and agitation (300 r.p.m.). These media contained 2.0% of glycerol, 2.0% of soybean meal and 0.3% of NaCl and had an adjusted pH of 7.0. The media were sterilized at a temperature of 120° C. for 15 minutes before use. After completion of the fermentation, the pH of the cultured broths was 4.8 and an inhibition zone against *Mycoplasma gallisepticum* (diameter—30 mm) was observed in the supernatant of the broths. The broths (20 liters) were subjected to centrifugation to remove the mycelium. The filtrate was adjusted to a pH of 2.0 with 6N HCl and was then subjected to extraction with butyl acetate (4 liters). The butyl acetate layer was extracted with 1% sodium bicarbonate aqueous solution (800 ml). The aqueous layer was adjusted to a pH of 2.0 with 6N HCl and was subjected to extraction with ethyl acetate. The ethyl acetate layer was concentrated and added with petroleum ether to give yellow-brown powders (1.09 g) which were further purified in the following manner.

The crude powders containing nanaomycins A and B were dissolved in ethyl acetate (15 ml) and added with silica-gel (4 g) and then concentrated in vacuo to dryness. The dried material was transferred to a column packed with silica gel (55 g) and then developed with a solvent system of benzene-ethyl acetate (4:1 v/v). The eluate was divided into individual fractions (each 15 ml). Each fraction was then assayed by the above-described paper disc method using *Mycoplasma gallisepticum* KP-13 as a test microorganism. The first part of the eluate, i.e. Nos. 8 to 22 of the fractions contained nanaomycin A, and No. 14 exhibited a highest activity against the test microorganism. For fractions after No. 30, another solvent system of benzene-ethyl acetate (3:1 v/v) was used as the eluting solution. Nos. 32 to 60 of the divided fractions contained nanaomycin B, and the activity of No. 46 was highest against the control microorganism. The fractions Nos. 8 to 22 were combined and concentrated in vacuo to dryness. The dried solid material was dissolved in ethanol and then added with a small amount of water to give yellow needle crystals (31.7 mg). The crystals were recrystallized from an ethanol solution in a similar manner to that described above to give a purified nanaomycin A (25.3 mg; purity: more than 99%; melting point: 178°–180° C).

UV absorption spectrum of nanaomycin A: $\lambda_{max}^{MeOH}$ nm: 250, 274 and 423

IR absorption spectrum of nanaomycin A:

Characteristic strong absorptions at 1725, 1640 and 1610 cm$^{-1}$ when measured by KBr method.

The second part of the fractions (Nos. 32 to 60) was combined and concentrated in vacuo to dryness to give pale yellow powders (450 mg). The powders were further subjected to column chromatography using silica gel in a similar manner to that described above to obtain purified powders of nanaomycin B (270 mg; purity: 99%; melting point: 84°–86° C.).

UV absorption spectrum of nanaomycin B: $\lambda_{max.}^{MeOH}$ nm: 231 and 352

IR absorption spectrum of nanaomycin B:

Characteristic strong absorptions at 1705, 1648 and 1605 cm$^-$when measured by KBr method.

EXAMPLE 2:

To the solid material which was obtained by centrifugation of the cultured broths prepared in a similar manner to that described in Example 1, there was added ethyl acetate (5 liters) with agitation. The thus-obtained extract was added with 1% solution of sodium bicarbonate (2 liters) to transfer the material including nanaomycins A and B to the aqueous layer. The aqueous layer was adjusted to a pH of 2.0 with hydrochloric acid and was then subjected to extraction with ethyl acetate (500 ml). The extracted solution was concentrated in vacuo to dryness to give crude powders (521 mg) in yellow brown. The powders were subjected to silica gel column chromatography and the eluate was treated to obtain nanaomycins A and B in a similar manner to that described in Example 1.

|  | Yield | Melting Point | Purity |
| --- | --- | --- | --- |
| Nanaomycin A | 13 mg | 173–175° C. | 95% |
| Nanaomycin B | 85 mg | 82–84° C. | 92% |

What is claimed is:

1. A process for producing nanaomycin B by fermentation which comprises the steps of culturing *Streptomyces rosa var. notoensis* in a medium containing carbon sources, nitrogen sources and inorganic substances at a temperature of from 15° to 40° C. and a pH of 6 to 10 for about 2 to 8 days, and recovering as the principal product accumulated nanaomycin B from the cultured broth.

2. A process for producing nanaomycin B by fermentation comprising the steps of culturing aerobically a micro-organism belonging to the genus *Streptomyces rosa var. notoensis* in a medium containing a carbon source, a nitrogen source, and an inorganic substance source, and recovering from the culture broth as principal product the accumulated nanaomycin B.

3. A process of claim 2, in which the strain is *Streptomyces rosa var. notoensis* (FERM-P No. 2209).

4. A process of claim 2, in which the culturing is carried out at a temperature of from 15° to 40° C. at a pH of 6–10 for about 2–8 days.

* * * * *